(12) United States Patent
Hartnick et al.

(10) Patent No.: US 8,276,589 B2
(45) Date of Patent: Oct. 2, 2012

(54) CRICOTHYROTOMY DEVICE

(75) Inventors: Christopher J. Hartnick, Newton, MA (US); Michael Cunningham, Lexington, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 1019 days.

(21) Appl. No.: 11/963,535

(22) Filed: Dec. 21, 2007

(65) Prior Publication Data
US 2009/0159086 A1  Jun. 25, 2009

(51) Int. Cl.
*A61M 16/00* (2006.01)
(52) U.S. Cl. ......... 128/207.29; 128/200.24; 128/207.14; 128/200.26
(58) Field of Classification Search ............. 128/200.24, 128/200.26, 205.19, 207.14–207.29, 912, 128/DIG. 26; 606/185; 604/165.02, 165.04, 604/167.01, 246, 247, 256, 535, 121, 124–125, 604/181, 187; D24/130, 112
See application file for complete search history.

(56) References Cited

U.S. PATENT DOCUMENTS

| | | | |
|---|---|---|---|
| 1,950,137 A | | 3/1934 | Dowe |
| 3,688,773 A | * | 9/1972 | Sol Weiss ................ 128/207.29 |
| 3,766,916 A | * | 10/1973 | Moorehead et al. ..... 604/165.04 |
| 3,817,250 A | * | 6/1974 | Weiss et al. ............. 128/207.29 |
| 3,934,576 A | * | 1/1976 | Danielsson .................. 600/487 |
| 4,096,860 A | * | 6/1978 | McLaughlin .................. 604/44 |
| 4,212,297 A | * | 7/1980 | Johnson et al. .......... 128/207.14 |
| 4,231,367 A | * | 11/1980 | Rash ........................ 604/165.02 |
| 4,622,968 A | * | 11/1986 | Persson .................... 604/165.01 |
| 4,655,747 A | | 4/1987 | Allen, Jr. |
| 4,838,870 A | * | 6/1989 | Haber et al. .................. 604/187 |
| 4,889,112 A | * | 12/1989 | Schachner et al. ........ 128/200.26 |
| 5,009,251 A | * | 4/1991 | Pike et al. ................ 137/599.06 |
| 5,032,117 A | | 7/1991 | Motta |
| 5,057,093 A | * | 10/1991 | Clegg et al. ................... 604/535 |
| 5,058,580 A | | 10/1991 | Hazard |
| 5,090,408 A | * | 2/1992 | Spofford et al. ......... 128/207.14 |
| 5,097,410 A | * | 3/1992 | Hester et al. .................... 710/31 |
| 5,098,405 A | * | 3/1992 | Peterson et al. ............. 604/247 |
| 5,181,509 A | | 1/1993 | Spofford et al. |
| 5,186,168 A | | 2/1993 | Spofford et al. |
| 5,217,005 A | | 6/1993 | Weinstein |
| 5,297,546 A | | 3/1994 | Spofford et al. |
| 5,300,034 A | * | 4/1994 | Behnke et al. ............ 604/167.02 |
| 5,301,682 A | * | 4/1994 | Debbas ......................... 600/550 |
| 5,409,465 A | * | 4/1995 | Boggs et al. .................. 604/191 |
| 5,445,645 A | * | 8/1995 | Debbas ......................... 606/192 |

(Continued)

OTHER PUBLICATIONS

Rüsch Quick Trach®, Emergency Cricothyrotomy, Product # 120900040 & 120900020. [online]. Teleflex Medical, Durham, NC [retrieved on Feb. 21, 2008]. Retrieved from the Internet: <URL: http://www.myrusch.com/images/rusch/docs/A40S.pdf>, 1 p.

*Primary Examiner* — Annette Dixon
(74) *Attorney, Agent, or Firm* — Fish & Richardson P.C.

(57) ABSTRACT

A cricothyrotomy syringe has a hollow body, a needle connector at an end of the body, an aperture at an opposite end of the body, a plunger in the aperture, the plunger having a seal that forms a liquid tight seal with an inner surface of the body and the plunger moveable within the body between an extended position and a compressed position and a ventilator adaptor extending from a side of the body, where an interior of the ventilator adaptor is in fluid communication with an interior of the body when the plunger is in the extended position.

21 Claims, 6 Drawing Sheets

U.S. PATENT DOCUMENTS

| | | | |
|---|---|---|---|
| 5,496,284 A | 3/1996 | Waldenburg | |
| 5,653,230 A * | 8/1997 | Ciaglia et al. | 128/207.15 |
| 5,662,674 A * | 9/1997 | Debbas | 606/192 |
| 5,665,074 A * | 9/1997 | Kelly | 604/247 |
| 5,690,669 A | 11/1997 | Sauer et al. | |
| 5,707,352 A | 1/1998 | Sekins et al. | |
| 6,017,327 A * | 1/2000 | Wiklund | 604/167.01 |
| 6,029,657 A | 2/2000 | Century | |
| 6,056,727 A | 5/2000 | O'Neil | |
| 6,387,077 B1 * | 5/2002 | Klibanov et al. | 604/181 |
| 6,398,761 B1 | 6/2002 | Bills et al. | |
| 6,553,993 B2 * | 4/2003 | Toti et al. | 128/207.14 |
| 6,602,229 B2 * | 8/2003 | Coss | 604/187 |
| 6,630,126 B2 | 10/2003 | Driehuys et al. | |
| 7,618,412 B2 * | 11/2009 | Chernack | 604/890.1 |
| 7,780,649 B2 * | 8/2010 | Shippert | 604/542 |
| 7,789,872 B2 * | 9/2010 | Shippert | 604/542 |
| 7,794,449 B2 * | 9/2010 | Shippert | 604/542 |

* cited by examiner

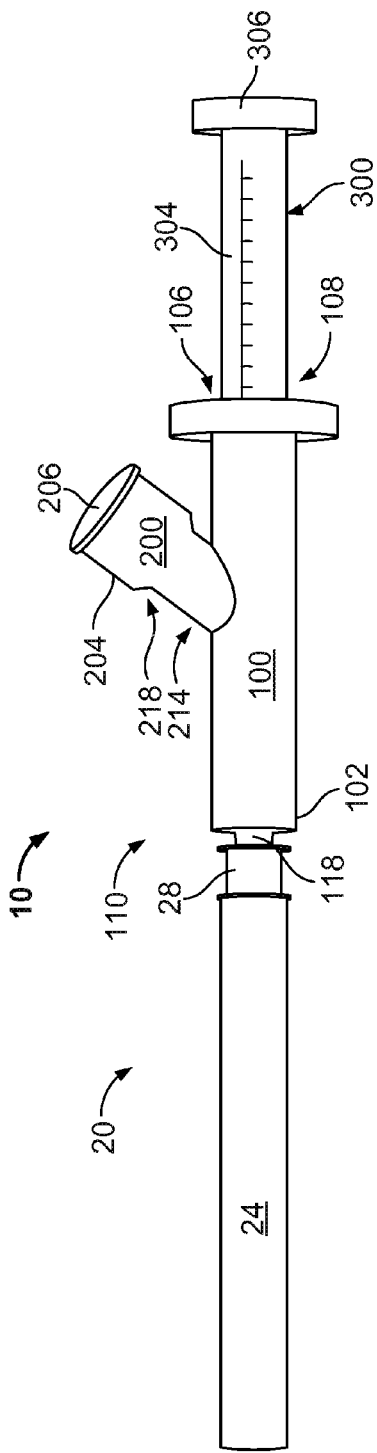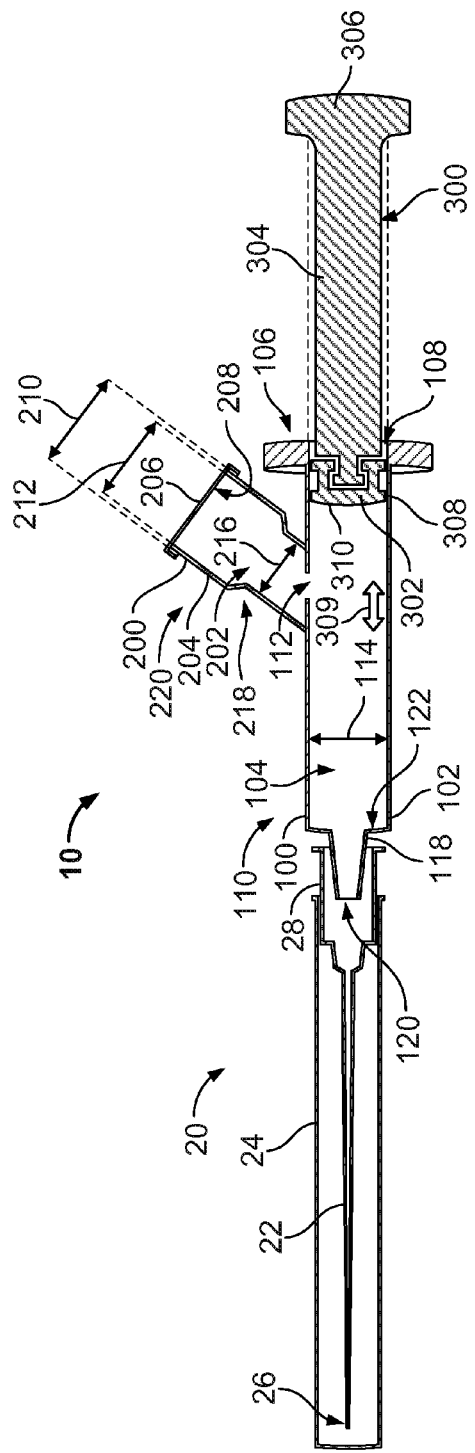

CRICOTHYROTOMY DEVICE

TECHNICAL FIELD

This document relates to medical devices used for establishing an airway.

BACKGROUND

Establishing an airway in a patient in acute airway distress is often the first step in treating a patient under an advanced cardiac life support protocol. The patient's airway can be secured using mask ventilation, endotracheal intubation or tracheotomy, as most suitable for the situation. In certain circumstances, these three established modalities of safely establishing an airway may be difficult to accomplish in a timely fashion. In some emergency situations, these three options are not available to a treating practitioner, either due to the reason for which the patient's airway is obstructed or lack of available proper medical equipment. Under such circumstances some practitioners use what can be referred to as needle cricothyrotomy. This involves inserting a needle attached to a syringe into the patient's trachea to establish an airway. The efficacy of this technique is limited, however, as there is no readily available means of connecting the syringe to a ventilation device. The creation of such a connection takes valuable time away from the emergency task at hand, and even once established, air is not easily delivered through the needle to the patient's airway. Devices for quickly and easily establishing an airway for delivering oxygen to the patient are therefore desirable.

SUMMARY

Described herein are syringe assemblies for performing cricothyrotomy procedures.

In one embodiment, a medical device for establishing an airway is described. The device includes a syringe comprising a hollow body, a needle connector at an end of the body, an aperture at an opposite end of the body, a plunger in the aperture, the plunger having a seal that forms a liquid tight seal with an inner surface of the body and being moveable within the body between an extended position and a compressed position and a ventilator adaptor extending from a side of the body, wherein an interior of the ventilator adaptor is in fluid communication with an interior of the body when the plunger is in the extended position.

Embodiments of the device may include one or more of the following features. The ventilator adaptor can be closer to the aperture than to the needle connector. The ventilator adaptor can be in an upper one-third of the body. The ventilator adaptor is for a 3.0 inner diameter endotracheal tube, a 2.5 inner diameter endotracheal tube, a 2.0 diameter endotracheal tube. A flexible sheath can surround a portion of the body and a portion of the ventilator adaptor. A cap can be on the ventilator adaptor. The ventilator adaptor can be at between about a 30° and 90° angle to a main axis of the body, such as at about a 45° angle to a main axis of the body. The ventilator adaptor can have a tapered portion. The needle connector can be a luer lock connector. A portion of the adaptor closest to the body can be formed of a rigid material. A flange can surround the aperture. The body can be capable of holding 5 cc of fluid. The body can be formed of plastic. The body can be a right cylinder. A valve can be between the hollow body and the needle connector. The valve can be a three way valve. The device can include a needle connected to the body at the needle connector.

The device can be used as follows. The needle is inserted into a trachea of a patient with a blocked airway, wherein the syringe is filled with a liquid. The plunger is pulled toward the extended position. Whether bubbles appear in the liquid is determined. If bubbles appear in the liquid, the liquid is expelled from the syringe. After expelling the liquid from the syringe, the plunger is pulled toward the extended position to a position where the interior of the ventilator adaptor is in fluid communication with an interior of the needle. After determining that bubbles appear in the liquid, a ventilator device is attached to the ventilator adaptor.

Embodiments of the devices described herein may include one or more of the following advantages. The devices described herein can be made available in a variety of treatment facilities, such as emergency rooms or vehicles, doctor's offices and first responder kits. The devices can be inexpensive and disposable, so that a treating practitioner is more likely to have the device available for use. The devices can obviate the need for a practitioner to create a device out of various parts, which can save time and thus potentially improve a patient's chance of survival and even save his or her life.

The device can be included in a kit. The kit can also include one or more of a blade, a French flexible suction catheter, disinfectant, sutures, a disposable bipolar electrosurgical handpiece, a disposable unipolar electrosurgical handpiece, electrosurgical tip cleaner, a spatula, a needle, pack peanuts, a syringe or a solution of lidocaine with epinephrine.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 is a top view of a cricothyrotomy syringe.

FIG. 2 is a cross-sectional view of a cricothyrotomy syringe in an extended configuration.

DETAILED DESCRIPTION OF ILLUSTRATIVE EMBODIMENTS

Figure 3:
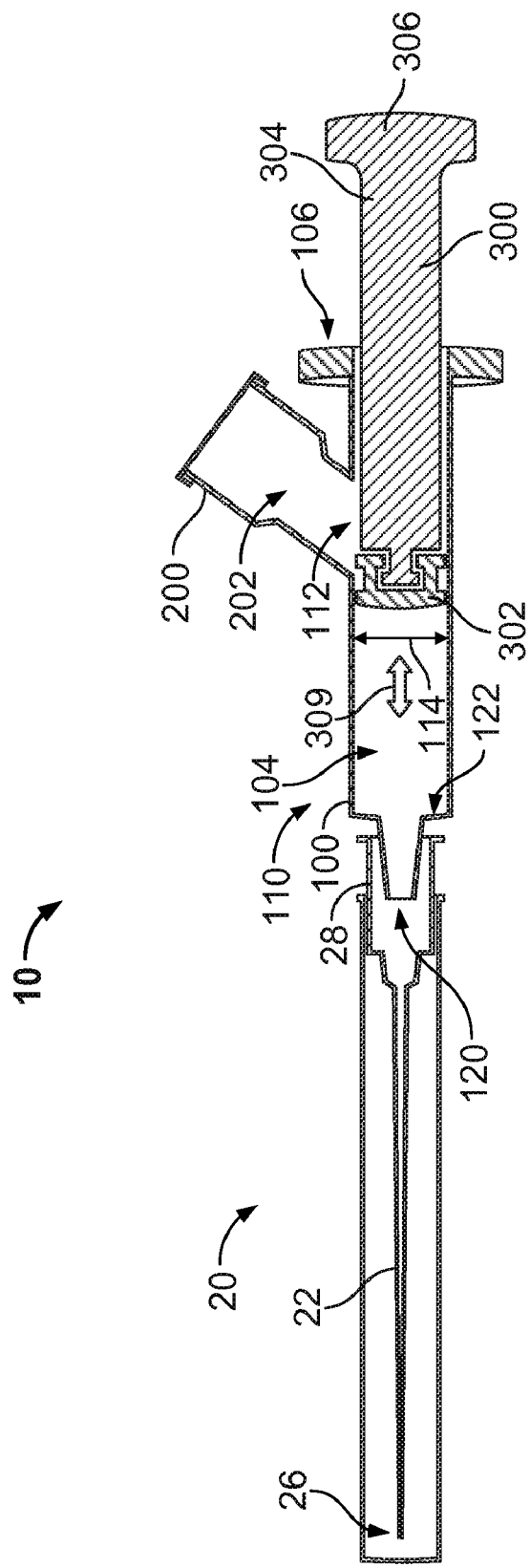
FIG. 3 is a cross-sectional view of a cricothyrotomy syringe in a compressed configuration.

Referring to FIGS. 1-2, a cricothyrotomy syringe 10 includes a syringe body 100, which can be tubular in shape, a ventilator adaptor 200 that is configured to connect to a ventilator, such as to a tube extending from the ventilator, and a plunger 300 for moving fluid, such as saline or air, in and/or out of the syringe 10. The syringe body 100 includes an exterior wall 102, such as a cylindrical wall, that defines an interior volume 104, a proximal end 106 that includes a proximal aperture 108, a side aperture 112, and a distal end 110 that is configured to removably couple to a needle assembly 20. The ventilator adaptor 200 is connected to the body at aperture 112.

The plunger 300 includes a seal 302, an extension shaft 304 and handle 306. The handle 306 can be a flange that extends out from the shaft 304. The seal 302 can include one or more annular seal rings 308 with outer diameters that are the same size or just slightly larger as an inner diameter 114 of the interior volume 104, thus allowing the seal 302 to form a moveable fluid-tight connection between the plunger 300 and the syringe body 100. This allows the plunger 300 to move through the interior volume 104 in the lengthwise directions (indicated by arrows 309) while not allowing fluid to pass between the exterior wall 102 and the seal 302. The seal 302 can be formed of a compliant material which is compressible or bendable in order to form the fluid tight seal, even when there is a slight defect on the interior of the syringe body 100.

The distal end 110 of the syringe body 100 includes a needle adaptor 118 (e.g., a male luer fitting) with a distal aperture 120 that can be used to removably couple the syringe body 100 to the needle assembly 20. The needle assembly 20 includes a needle 22 (e.g., an 18 gauge needle) that can be used for penetrating the tissue of a patient, a syringe adaptor 28 (e.g., a female luer lock fitting) for mating with the needle adaptor 118 and a needle cap 24 that surrounds the needle 22, thus protecting it from damage and from inadvertently coming into contact with a user. The needle cap 24 can remain in place until the needle assembly is coupled to the syringe body 100 and the syringe 10 is ready to use. The needle assembly 20 is optionally included with the syringe 10. Stand alone needles can provide the practitioner with more flexibility in selecting the desired gauge of needle to use with the syringe 10.

The side aperture 112 in the exterior wall 102 fluidly connects the interior volume 104 of the syringe body 100 to an interior volume 202 of the ventilator adaptor 200. The ventilator adaptor 200 includes a cylindrical exterior wall 204 connected to the exterior wall 102 of the syringe body 100 and can include a removable cap 206 which seals an aperture 208 located at the end of the ventilator adapter 200. The cylindrical exterior wall 204 is of a size that is universally applicable connecting to ventilation devices. The ventilator adaptor is sized similarly to an adaptor available from Teleflex Medical, Research Triangle Park, NC. The cap 206 can be configured to seal fluid, e.g., air or liquid, from leaking out of or leaking into the interior volume 202 through the aperture 208. Furthermore, the cap 206 can be configured (e.g., pressure fit) such that when the syringe 10 is pressurized (e.g., by pushing the plunger 300 into the syringe body 100), the pressure will not cause the cap 206 to leak and/or disconnect from the adapter 200.

In some embodiments, the ventilator adapter 200 has an end portion 220 having an outer diameter 210 (e.g., 18 mm) and an inner diameter 212 (e.g., 15 mm) and a connecting portion 214 with an inner diameter 216. The connecting portion can have an inner diameter of 2.5 mm, 3.0 mm, 3.5 mm, 4.5 mm, 5.0 mm or other suitable size. In some embodiments, the inner diameter 212 of part of the adapter 210 is larger than the inner diameter 114 of the syringe body 100. The adapter 200 can include a transition portion 218 where the inner diameter tapers from the inner diameter 212 of an end portion 220 to the inner diameter 216 of the connecting portion 214. In other embodiments, the inner diameter 212 can be the same size or smaller than the diameter 114 of the syringe body 100.

In some embodiments, the adaptor 200 has a central axis that is at an angle to a central axis of the syringe body 100, such as at an angle of between about 30° and 90°, such as about 45° or about 60°. The adaptor 200 can be closer to the proximal end 106 of the syringe body 100 than to the distal end 110, such as within the upper half of the syringe body 100 or within the upper third of the syringe body 100, assuming the proximal end 108 is the top of the syringe body. Placing the adaptor 200 closer to this end of the syringe body 100 facilitates the use of the syringe for particular procedures, described further below. Both the syringe body 100 and the ventilator adaptor 200 can be formed of substantially rigid material which prevents the airway from being blocked due to a bend in the syringe 10.

In some embodiments, the needle 22 is inserted into a trachea of a patient with a blocked airway when the syringe 10 is filled with a liquid, e.g., saline. The plunger 300 is initially in a partially compressed configuration, such as that shown in FIG. 3. The compressed configuration is when the seal 302 on the plunger is close to the distal end 110 of the syringe body 100 and the extended position is when the seal 302 is closer to the proximal end 106 of the syringe body 100. The plunger 300 can be pulled toward the extended position (FIG. 2) and the syringe body 100 can be inspected to determine whether bubbles appear in the liquid. If bubbles appear in the liquid, the syringe body 100 can be detached from the needle 22 and the liquid expelled from the syringe, followed by reattachment of the syringe 100 to the needle 22. After expelling the liquid from the syringe body 100, the plunger 300 can be pulled toward the extended position to a position where the interior volume 202 of the ventilator adaptor 200 is in fluid communication with an interior of the needle assembly, that is, so that the seal 302 on the plunger 300 does not block fluid from moving from the adaptor interior volume 202 to the syringe body 100. The tubing of a ventilator device can be attached to the ventilator adapter 200 either before the syringe body 100 is reattached to the needle 22 or after.

In some embodiments, the proximal aperture 108 of the syringe body 100 has substantially the same inner diameter as the inner diameter 114 of the interior volume 104, such that the included plunger 300 can travel through the interior volume 104 and be removed from the proximal aperture 108.

Figure 4:
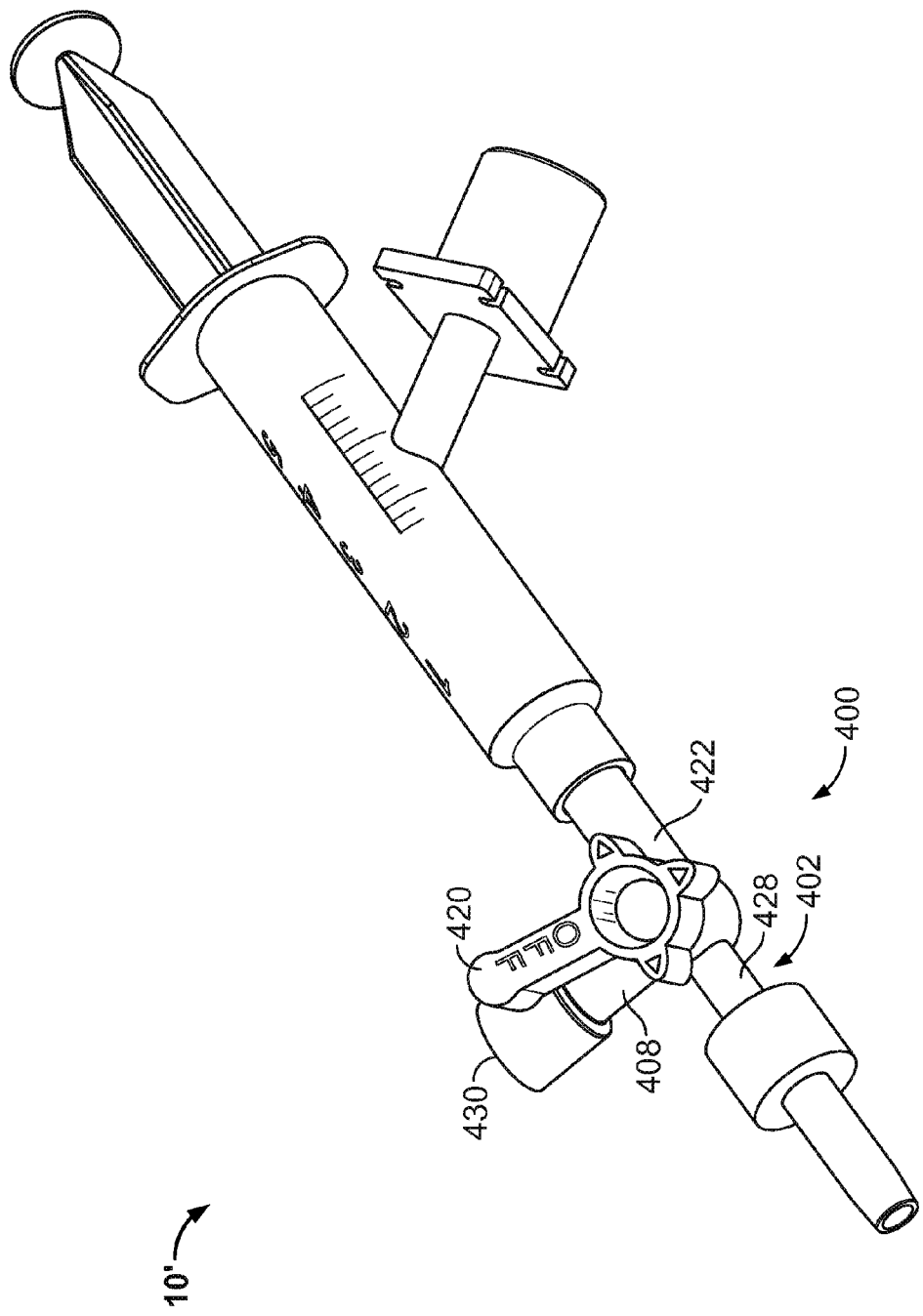
FIGS. 4-6 are representations of alternative embodiments of a cricothyrotomy syringe.

Referring to FIG. 4, in some embodiments a cricothyrotomy syringe 10' includes a stopcock located between the syringe body 100 and the needle 22. A stopcock portion 400 extends from the end of the syringe body 100. In some embodiments, a main lumen 402 of the stopcock portion 400 is coaxial with the syringe body 100. A side lumen 404 extends from the main lumen 402, such as at a right angle to the main lumen 402. A proximal portion 422 of the main lumen is between the side lumen 404 and the syringe body 100 and a distal portion 428 of the main lumen 402 is between the side lumen 404 and the needle (not shown). A valve 420 is between the proximal portion 422 and the distal portion 428, in some embodiments overlapping the junction of the main lumen 402 and the side lumen 404. The valve 420 is able to block off flow in some positions. A suitable type of stopcock portion 400, such as 9 Fr Hi-Flo stopcock 4 way with fixed M L/L (W20058 or R20386) is available from Arrow Walrus, in Woburn, Mass. Using the valve depicted, both portions 422, 428 of the main lumen 402 can be in fluid connection with the side lumen 404, the proximal portion 422 can be blocked from side branch 404 and the distal portion 428, the side lumen 404 can be blocked off from the main lumen 402 or the distal portion 428 can be blocked off from the side lumen 404 and proximal portion 422. The valve 420 shown is a rotating type valve, however other types of valves can also be used. A cap 430 is optionally provided for sealing off the side lumen 404. A cover (not shown) can also be provided for sealing off the distal portion 428 of the main lumen 402 when the needle is not connected to the assembly. The distal portion 428 has an end configured for attaching to a needle.

Figure 5:
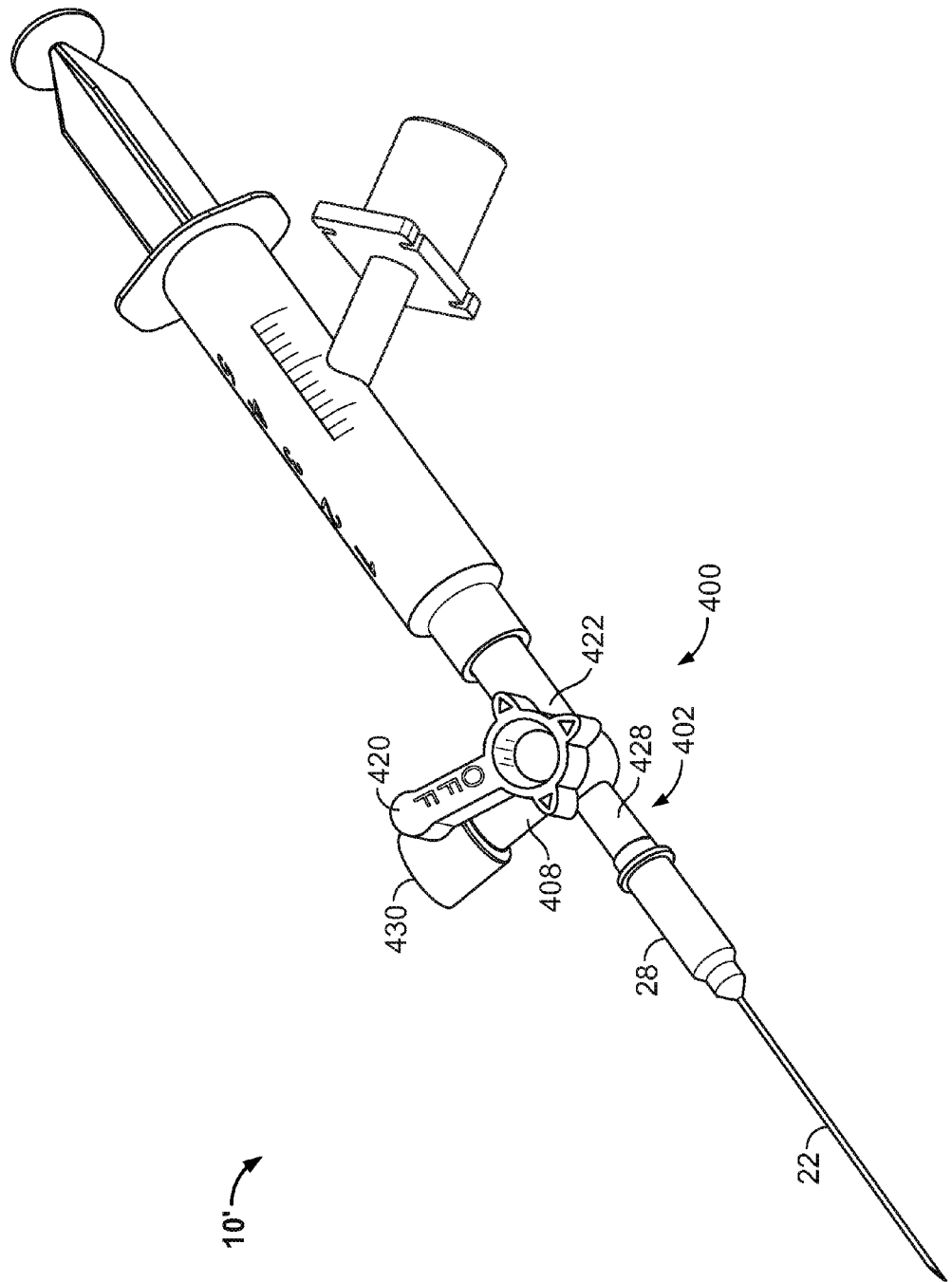

Referring to FIG. 5, a cricothyrotomy syringe 10' with a stopcock portion 400 between the syringe body 100 and needle 22 is shown.

Figure 6:
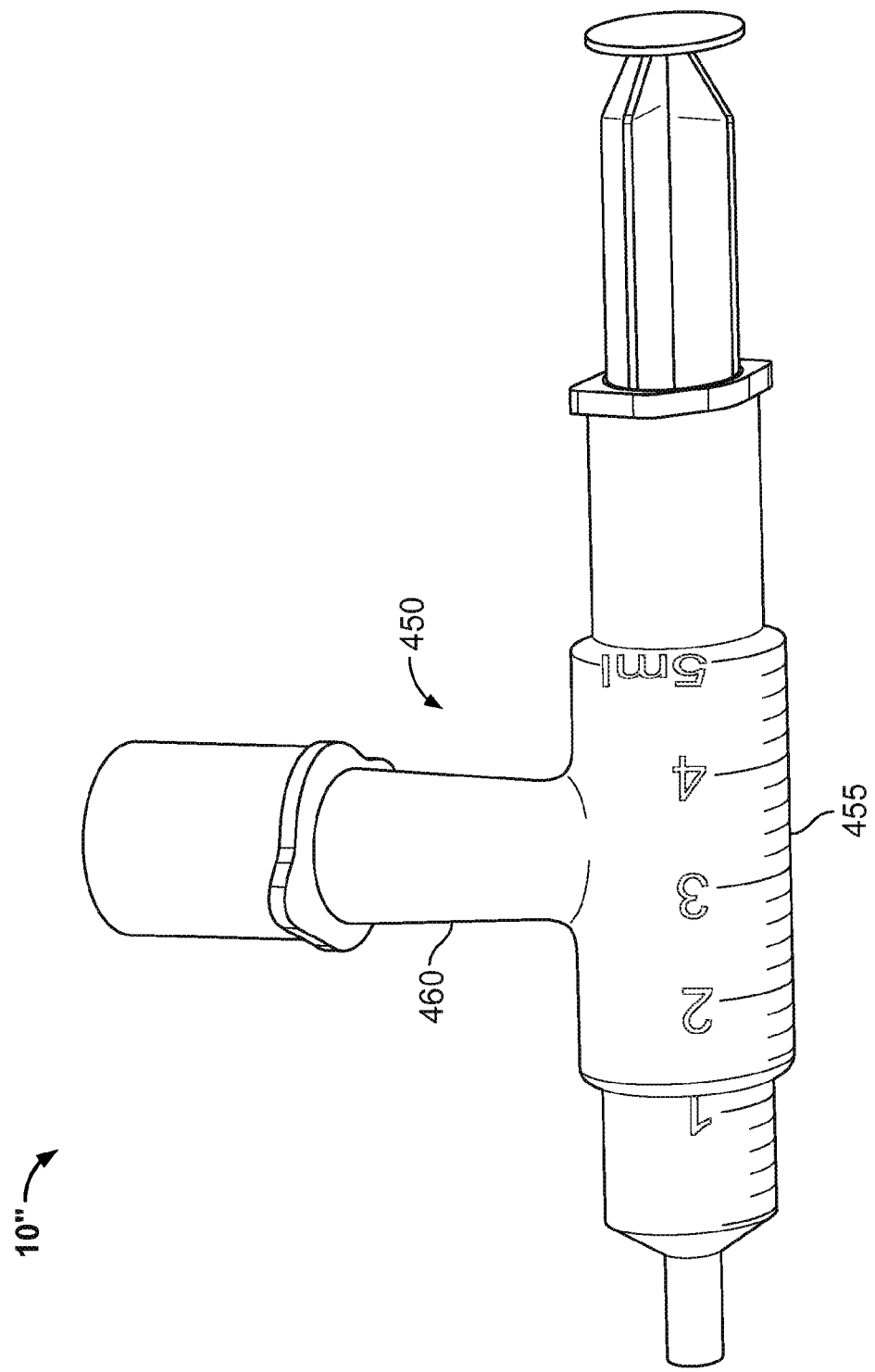
Figure 7:
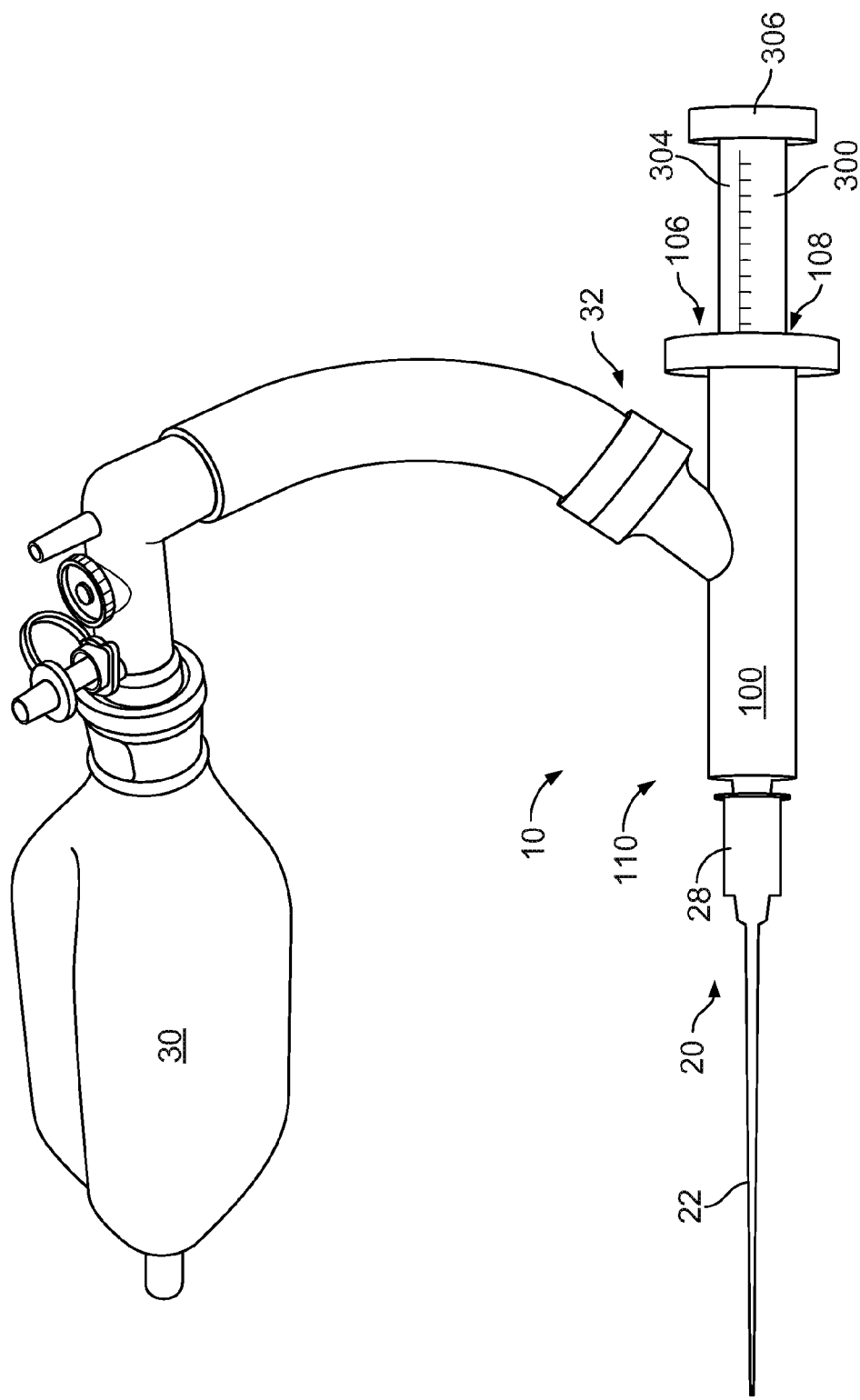
FIG. 7 is representation of a cricothyrotomy syringe connected to a ventilator bag.

Referring to FIG. 6, in some embodiments a cricothyrotomy syringe 10" has a sheath 450 provided over the syringe body 100. The sheath can be t-shaped, where main straight portion 455 surrounds the syringe body 100. A branch portion 460 extends at an angle, such as a 45° or 90° angle, from the straight portion 455. The syringe body 100 has an aperture that is aligned with the branch portion 460 of the sheath 450 so that the interior of the syringe body can be in fluid communication with an interior of the sheath 450. The adaptor 200 fits into an end of the branch portion 460. A liquid tight seal is formed between the sheath 450 and the exterior of the syringe body 455 as well as between the sheath 450 and the adaptor 200. In some embodiments, the sheath 450 is flexible or malleable. When pressure is applied to the sheath, such as when a device is being attached to the adaptor 200, a flexible or malleable sheath allows the connection between the adaptor 200 and the syringe body 100 to be sufficiently flexible so that the junction region is able to bend while providing integrity to the joint between the syringe body 100 and the adaptor 200. A flexible sheath can be formed of a material that bends under stress without cracking or breaking, such as silicone. The flexible sheath may stretch and can return to its pre-bent position without any permanent deformation caused by the bending action. An exemplary flexible sheath is a Montgomery T-tube. Because the syringe, sheath and adaptor can be formed of different materials to achieve different properties, such as stiffness, the three components can either be permanently attached to one another or removably connected to one another.

In some embodiments, the syringe 10 can include a stainless steel material (e.g., 316L stainless steel), glass, plastic (e.g., polyethylene), and/or other materials suitable for use in medical devices and/or medical syringes. Because the syringe body 100 and plunger 300 can be disposable, polymers suitable for use in medical devices (e.g., polypropylene, polyvinyl chloride, polyimide, polyamide, polyamide-imide, acrylic or polycarbonate) can be used in the manufacture of the syringe 10. The syringe 10 can be manufactured in a plurality of sizes to be used on patients of varying sizes (e.g., infants, adolescents or adults). In some embodiments, the syringe 10 is designed to be used with infants and as such has an overall size similar to that of a 3.0 ml syringe. Other exemplary embodiments have an overall size similar to that of a 5.0 ml syringe.

In some embodiments, the syringe 10 may come ready to use in a hermetically sealed package to keep the syringe 10 sterile until used. The syringe can be used to establish a temporary airway in a patient. As such, the syringe 10 includes the needle 22 for penetrating a trachea and surrounding tissue, the adapter 200 for connection to, for example, an anesthetic ventilator, and a fluid path between the adapter 200 and the needle 22 to allow for the delivery of air from the attached ventilator to the trachea and subsequently to the lungs of the patient. As it may be desirable to interrupt the fluid path between the adapter 200 and the needle 22, the syringe 10 can be configured such that the fluid path can be interrupted by changing the position of the plunger 300. For example, as depicted in FIG. 2, when the plunger 300 is positioned such that the seal 302 is located between the side aperture 112 and the proximal aperture 108, the interior volume 104 of the syringe body 100 is fluidly connected to the interior volume 202 of the ventilator adaptor 200, while fluid is blocked by the seal 302 from entering the interior volume 104 through the proximal aperture 108. When the plunger 300 is positioned such that the seal 302 is located between the side aperture 112 and the distal aperture 120, the interior volume 104 is not fluidly connected to the interior volume 202, while fluid is still blocked by the seal 302 from entering the interior volume 104 through the proximal aperture 108.

Referring back to FIG. 3, when the plunger 300 is inserted into the syringe body 100 such that the seal 302 is located between the side aperture 112 and the distal end 110 of the syringe body 100, the interior volume 104 of the syringe body 100 is effectively isolated from the interior volume 202 of the adapter 200. When in this configuration, movement of the plunger 300 toward or away from the distal end 110 can cause an increase or decrease in pressure on the contents of the interior volume 104 of the syringe 10 and/or cause material to be expelled or drawn into the interior space 104 (e.g., through the distal aperture 120 and/or the needle 22). One exemplary function of the syringe 10 in this configuration is for performing a "bubble test". To verify that a distal tip 26 of the needle 22 is properly positioned within a trachea, a fluid such as sterile saline is drawn into the interior volume 104 of the syringe 10 prior to placement of the needle 22 in the trachea. Once the needle 22 is in place, the plunger 300 can be withdrawn slightly from the syringe body 100 creating a vacuum in the interior volume 104. If air is drawn with minimal resistance into the interior volume 104 through the needle 22, then the needle 22 is positioned correctly in an airway (e.g., the interior space of a trachea). Because the seal 302 is located between the side aperture 112 and the distal end 110, this "bubble test" can be performed without allowing air into the syringe body 100 through the adapter 200. Therefore, it is irrelevant whether the adapter 200 is sealed by the cap 206 or if the adapter 200 is connected to a ventilator. When it is desired that the interior volume 104 be fluidly connected to the interior volume 202, the plunger 300 can be withdrawn such that the seal 302 transitions to a location between the side aperture 112 and the proximal end 106.

As noted above, a "bubble test" can be performed when the needle 22 is placed within a trachea. After drawing air through the needle 22 into the interior volume 104 to confirm that the tip of the needle is inside the trachea, the syringe body 100 can be disconnected from the needle 22 and the saline can be forced out by pushing the plunger 300 until the front face 310 of the seal 302 contacts an interior face 122 of the distal end 110. The plunger 300 is pulled back until the seal 302 is located between the side aperture 112 and the proximal end 106 and the cap 206 is removed from the syringe body 100, allowing a ventilator device (e.g., a ventilator bag 30 as depicted in FIG. 6 or a mechanized ventilator) to be connected to the adapter 200 via a length of tubing 32. The syringe body 100 can be re-attached to the needle 22 and a ventilator can be connected to the ventilator adapter 200, resulting in the ventilator being fluidly connected to the interior space of a patient's trachea.

Referring back to FIG. 4, a stopcock on the syringe body allows the bubble test to be performed without separating the syringe from the needle body. When the needle is inserted into the patient, the stopcock can be in any position, but may be with the off portion closing off the distal portion of the stopcock. This can prevent from any saline being inadvertently released from the syringe body into the patient. Once the needle is believed to be in the airway, the valve can be positioned so that the side lumen is closed off and the main branch is in fluid communication with the syringe. Once air is drawn into the needle and the stopcock, possibly past the valve, the valve can be turned so that the off portion of the valve seals the distal portion of the stopcock from the syringe body. This allows the syringe body to be in fluid communication with the side lumen. The plunger is then depressed, which forces the saline out of the side lumen. Once the saline has been evacuated from the syringe body, the ventilator can be connected to the syringe body.

To facilitate performing emergency cricothyrotomies, the cricothyrotomy syringe can be a relatively low cost disposable item that can come sealed, either alone or as part of a kit. When packaged in a larger kit, the syringe can be part of an advanced life support airway kit used for establishing an airway. In an illustrative example, the syringe can be used in performing an emergency cricothyrotomy on a patient, such as a pediatric patient. In an emergency setting (e.g., in an emergency room, in a hospital room, or at the scene of an accident) a patient can suffer from a damaged airway such that a cricothyrotomy must be performed. When dealing with small patients with a limited cricothyroid space (e.g., pediatric patients or infants), a needle cricothyrotomy may be the preferred procedure. The cricothyrotomy syringe can advantageously be used for performing the needle cricothyrotomy and subsequently for ventilation.

Prior to use, the syringe can be removed from the packaging, a needle assembly can be attached to the syringe body, the needle cap can be removed, and the plunger is pressed all of the way into the syringe body until the front face of the seal contacts the interior face of the distal end on the syringe body. The distal tip of the needle can be submerged in sterile saline, followed by adding saline to the syringe by withdrawing the plunger. Alternatively, the needle can be attached after the syringe is loaded with saline. Once the syringe is prepared as described, a needle cricothyrotomy can be performed. For example, the needle tip is inserted in the cricothyroid space between the Adam's apple (i.e., thyroid cartilage) and the cricoid cartilage until the needle tip is located in the interior space of the patient's trachea. To verify that the tip is placed correctly, the bubble test is performed, which involves slightly withdrawing the plunger, e.g., as described above. If air bubbles up through the needle assembly into the syringe body, the tip is correctly placed. If air does not bubble up as described, the tip must be repositioned and the test repeated until air freely bubbles through the needle assembly into the syringe body.

Once the tip is positioned correctly, the syringe body is separated from the needle (e.g., by rotating the syringe body counterclockwise relative to the needle) leaving the needle in the cricothyroid space. The saline is expelled from the syringe by holding the syringe vertically, with the proximal end on top, and pressing on the plunger handle until the front face of the seal contacts the interior face of the distal end of the syringe body, thus emptying the syringe of its contents (e.g., saline). Once empty, the plunger handle can be pulled until the seal is located between the side aperture and the proximal aperture, thus fluidly connecting the interior volume of the syringe body to the interior volume of the ventilator adaptor. The syringe body is then re-attached to the needle. At this time, the cap can be removed from the ventilator adaptor, if there is a cap covering the opening to the adaptor. A ventilator or ventilation bag is attached to the syringe at the adaptive portion of the adaptor. Once the syringe is connected to a ventilator, the since syringe is connected to a needle and the needle tip is in the interior space of the trachea of a patient, the ventilator is fluidly connected to the interior space of the patient's trachea, thus allowing the ventilator to supply air, e.g., oxygen, and in some instances anesthetic, to the patient's lungs.

The syringe assembly described herein can be part of a kit of sterile supplies or accessories that are available in a location where a practitioner is likely to need or use the supplies. The kit can be useful in the event of a blocked airway event. The kit can include all of the following items or any combination the following items, in addition to the cricothyrotomy syringe assembly: two #15 blades, one each #6, 8, 10, 14 French flexible suction catheters, betadine solution or disinfectant prep sticks, two each #4-0 undyed monofilament sutures on a P-3 needle (18" or 45 cm) (to mature stoma), one each #3-0 braided (polyglactin 910) suture (54" or 135 cm) (for ligatures), two each #4-0 silk sutures on a P-3 needle (18" or 45 cm) or #4-0 pliable nylon black monofilament suture on a PC-3 needle (18" or 45 cm) (for stay sutures), a disposable bipolar electrosurgical handpiece and disposable unipolar electrosurgical handpiece, electrosurgical tip cleaner, one each insulated spatula and needle, insulated electrosurgical spatula and needle tips, one pack peanuts, 10 cc control syringe, a 25 ga 1.5 inch needle and 1% lidocaine with 1:100,000 epinephrine. Optionally, tracheotomy tubes can be included in the kit, such as multiple sizes for neonatal (3.0, 3.5, 4.0 and 4.5) and pediatric (3.0, 3.5, 4.0, 4.5, 5.0 and 5.5). Two of each tube can be included and the tubes may be cuff-free. A kit can contain three, four, five, six, seven, eight, nine, ten or more of the items.

A number of embodiments of the invention have been described. Nevertheless, it will be understood that various modifications may be made without departing from the spirit and scope of the invention. For example, although the syringe body has been described as tubular or as a right cylinder, it can take any shape that remains regular along its length, such as a tube with a oval, square or other cross section. Features of each of the embodiments described herein may be used together, even if not shown together. Accordingly, other embodiments are within the scope of the following claims.

What is claimed is:

1. A medical device for establishing an airway, comprising:
   a syringe comprising a hollow body;
   a needle connector at an end of the body;
   an aperture at an opposite end of the body;
   a plunger in the aperture, the plunger having a seal that forms a liquid tight seal with an inner surface of the body, the plunger being moveable within the body between a first position and a second position; and
   a ventilator adaptor extending from a side of the body,
   wherein, when the plunger is in the second position, the seal of the plunger is disposed between the ventilator adaptor and the needle connector such that the seal limits fluid communication between an interior of the ventilator adaptor and an interior of the body; and
   wherein the ventilator adaptor is disposed between the seal of the plunger and the needle connector when the plunger is in the first position such that the interior of the ventilator adaptor is in fluid communication with interior of the body when the plunger is in the first position.

2. The device of claim 1, wherein the ventilator adaptor is closer to the aperture than to the needle connector.

3. The device of claim 2, wherein the ventilator adaptor is in an upper one-third of the body.

4. The device of claim 1, wherein the ventilator adaptor sized to receive a 3.0 mm inner diameter endotracheal tube.

5. The device of claim 1, wherein the ventilator adaptor sized to receive a 2.5 mm inner diameter endotracheal tube.

6. The device of claim 1, wherein the ventilator adaptor sized to receive a 2.0 mm inner diameter endotracheal tube.

7. The device of claim 1, further comprising a cap on the ventilator adaptor.

8. The device of claim 1, wherein the ventilator adaptor is at about a 45° angle to a main axis of the body.

9. The device of claim 1, wherein the ventilator adaptor is between about a 30° and 90° angle to a main axis of the body.

10. The device of claim 1, wherein the ventilator adaptor has a tapered portion.

11. The device of claim 1, wherein the needle connector is a luer lock connector.

12. The device of claim 1, wherein a portion of the ventilator adaptor closest to the body is formed of a rigid material.

13. The device of claim 1, further comprising a flange surrounding the aperture.

14. The device of claim 1, wherein the body is capable of holding 5 cc of fluid.

15. The device of claim 1, wherein the body is formed of plastic.

16. The device of claim 1, wherein the body is a right cylinder.

17. The device of claim 1, further comprising a valve between the hollow body and the needle connector.

18. The device of claim 17, wherein the valve is a three way valve.

19. The device of claim 1, further comprising a needle connected to the body at the needle connector.

20. A method of using the device of claim 19, comprising:
inserting the needle into a trachea of a patient with a blocked airway, wherein the syringe is filled with a liquid;
pulling the plunger toward the first position;
determining whether bubbles appear in the liquid;
if bubbles appear in the liquid, expelling the liquid from the syringe;
after expelling the liquid from the syringe, pulling the plunger toward the first position to place the interior of the ventilator adaptor in fluid communication with an interior of the needle; and
after determining that bubbles appear in the liquid, attaching a ventilator device to the ventilator adaptor.

21. A kit, comprising:
the device of claim 1; and
one or more of a blade, a French flexible suction catheter, disinfectant, sutures, a disposable bipolar electrosurgical handpiece, a disposable unipolar electrosurgical handpiece, electrosurgical tip cleaner, a spatula, a needle, pack peanuts, a syringe or a solution of lidocaine with epinephrine.

* * * * *

UNITED STATES PATENT AND TRADEMARK OFFICE
CERTIFICATE OF CORRECTION

| | | |
|---|---|---|
| PATENT NO. | : 8,276,589 B2 | Page 1 of 1 |
| APPLICATION NO. | : 11/963535 | |
| DATED | : October 2, 2012 | |
| INVENTOR(S) | : Hartnick et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1143 days.

Signed and Sealed this
Twenty-third Day of September, 2014

Michelle K. Lee
*Deputy Director of the United States Patent and Trademark Office*